United States Patent
Chen et al.

[11] Patent Number: 6,060,423
[45] Date of Patent: May 9, 2000

[54] GROUP VIII METAL CATALYST ON A GALLIUM-ZINC OXIDE SUPPORT

[75] Inventors: Yu-Wen Chen; Sung-Cheng Hu, both of Chung-Li, Taiwan

[73] Assignee: Chinese Petroleum Corporation, Taipei, Taiwan

[21] Appl. No.: 09/296,658

[22] Filed: Apr. 23, 1999

[51] Int. Cl.[7] ............... B01J 23/06; B01J 23/08

[52] U.S. Cl. ............ 502/329; 502/325; 502/326; 502/327; 502/328; 502/332; 502/333; 502/334; 502/335; 502/336; 502/337; 502/338; 502/339

[58] Field of Search .................. 502/325, 326, 502/327, 328, 329, 332, 333, 334, 335, 336, 337, 338, 339

[56] References Cited

U.S. PATENT DOCUMENTS

| | | | |
|---|---|---|---|
| 4,543,347 | 9/1985 | Heyward et al. | 502/61 |
| 5,346,871 | 9/1994 | Robbins et al. | 502/61 |
| 5,736,114 | 4/1998 | Barthe et al. | 502/329 |
| 5,811,365 | 9/1998 | Barry | 502/343 |
| 5,899,678 | 5/1999 | Thomson et al. | 431/2 |

*Primary Examiner*—Elizabeth D. Wood
*Attorney, Agent, or Firm*—Bacon & Thomas

[57] ABSTRACT

A catalyst suitable for partially hydrogenating aromatic olefins to cyclohexene is disclosed. The catalyst is composed on a metallic active component deposited on a bi-oxide of gallium oxide-zinc oxide, and the metallic active component is selected from group VIII of the period table. The characteristic of the catalyst comprises a higher selectivity and yield in preparing cyclohexene.

8 Claims, No Drawings

GROUP VIII METAL CATALYST ON A GALLIUM-ZINC OXIDE SUPPORT

The present invention relates to a partial hydrogenating process for aromatic olefins from crude petroleum using a catalyst containing ruthenium. The process according to the present invention possesses a higher selectivity and yield in preparing cyclohexene, thus can be put into mass production of cyclohexene with an economical efficacy.

The double bond of cyclohexene possesses higher reacting activity, thus reacts easily with other materials. Therefore, cyclohexene is an excellent raw material for manufacturing pharmaceuticals, food, agrichemicals, animal feeds, specific chemicals, etc. According to the prior art, benzene can be partially hydrogenated to produce cyclohexene, cyclohexene can be hydrated to produce cyclohexanol, and cyclohexanol can be dehydrogenated to produce cyclohexanone. Additionally, cyclohexene can also be directly oxidized to adipic acid under suitable conditions. This process of preparing adipic acid is simpler than the conventional processes of using a cyclohexanone/cyclohexano mixture (KA-oil), thus can shorten the procedure of producing adipic acid. Therefore, this process is more economical. Adipic acid is the raw material for producing Nylon 66, and Nylon 66 is plastic material widely used in industry, for example it can be used in manufacturing various livelihood products, such as vehicle parts, athletic equipment, electronic products, etc.

As compared with traditional processes, for example the process of oxidation or pheno-hydrogenation of cyclohexane, the process of manufacturing cyclohexanol from benzene as the raw material (benzene to cyclohexene, then to cyclohexanol) is more economical because benzene is cheaper than cyclohexane, and the purification of the final product is simpler due to its higher selectivity. Although the reaction procedure and equipment of the process are more complex than those of traditional processes, the process is still more competitiveness than traditional ones.

Cyclohexene can be produced by many processes, such as the dehydrogenation and dehalogenation of halogenated alkanes, the dehydrogenation of cyclohexane and the dehydration of cyclohexanol. However, the above processes are more complex, thus their costs are higher. However, if adequate catalysts and reaction conditions can be applied, it is possible to synthesize cyclohexene from benzene by the hydrogenation process. This process is simpler than other ones, thus it is economical in industry. According to the equilibrium of thermal dynamics, the main product of hydrogenating benzene is cyclohexane ($C_6H_6 \flat C_6H_{12}$, $\Delta G°=-22$ KJ/mol; ($C_6H_{10} \flat C_6H_{12}$, $\Delta G°=-75$ KJ/mol; ($C_6H_6 \flat C_6H_{12}$, $\Delta G°=-97$ KJ/mol. The equilibrium of thermal dynamics is detrimental to the synthesis of cyclohexene if no adequate caytalysts and reaction conditions are applied. The yield of cyclohexene by partial hydrogenation of benzene is very low.

Generally, the catalysts suitable for the hydrogenation are noble metals or compounds containing them, which are deposited on adequate carriers. The activity and selectivity of the catalysts depend on the active components, the size of the catalytic particles, the distribution of catalytic particles, the reagents, the chemical adsorption of the products, etc. Generally, the catalysts are:

(1) Metal sulfides: the most popular catalysts of this type of compounds are molybdenum sulfide or tungsten sulfide. They are used in the hydrogenating-desulfuring reaction (HDS), hydrogenating-demetallizing reaction (HDM), hydrogenating-denitrogenating reaction (HDN), etc. of crude petroleum.

(2) Ironic catalyst: these catalysts comprise the elements selected from the first series of Group VIII of the Periodic Table, namely iron, cobalt and nickel. Nickel has a stronger hydrogenating ability, thus is widely used in industry. For example, Raney Nickel is a famous catalyst. From early times, nickel-containing catalyst have been used to selectively hydrogenate eatable oil so as to reduce the autooxidation of unsaturated bonds in the oil. However, nickel-containing catalysts require more critical reaction conditions in hydrogenating aromatic olefins.

(3) Nobel metallic catalyst: the second and third series of Group VIII of the Periodic Table, namely platinum (Pt), palladium (Pd), rhodium (Rh), iridium (Ir), ruthenium (Ru) and osmium (Os), wherein platinum (Pt), palladium (Pd), ruthenium (Ru) and rhodium (Rh) are more widely used. Although the catalytic activity of platinum and palladium is stronger than that of metal sulfide and ironic catalyst in hydrogenating reactions, they are easily poisoned with sulfur-or nitrogen-containing compounds, then lose their catalytic activity. The catalytic activity of palladium is worse than platinum, but its resistance to sulfide is better than platinum. However, the stability of palladium in the atmosphere of hydrogen at elevated temperature is worse than platinum. If platinum or palladium is used in the hydrogenation of benzene, the yield of cyclohexene is usually very low because the hydrogenating activity of the catalysts is not easily controlled.

According to the present invention, the catalyst used in the partial hydrogenation of benzene primarily comprises ruthenium because its cost is cheaper than platinum or palladium. In order to get higher product yield of cyclohexene, the reaction of over-hydrogenation to cyclohexane should be avoided. Thus, it is important how to appropriately adjust the hydrogenating ability of a catalyst and to maintain its active life. If the hydrogenating activity is too strong, benzene is over-hydrogenated to cyclohexane, and if the hydrogenating activity is too weak, the product yield of cyclohexene would be reduced and thus be uneconomical. Usually, a modifier is used to enhance the product yield if the yield is not high enough. The present catalyst is produced by depositing ruthenium on a carrier with an impregnating or vaporizing process. The characteristics of a catalyst primarily depend on the sintering and reducing process. Additionally, the chlorine ion, for example ruthenium chloride, and other impurities contained in the precursor may severely effect to the reacting activity and selectivity of the catalyst. During the procedures of producing the catalyst, the above reverse effects should be avoided if possible. In order to get the optimum reaction activity and selectivity, the physical and chemical properties should be especially considered. Ruthenium catalyst is sensitive to the above physical and chemical properties, such as specific surface, the distribution of pore size, the size and distribution of catalyst articles, active metal dispersion, crystallinity, carrier composition, hydrogen spill-over, minor modifier, etc.

The process of producing cyclohexene by partially hydrogenating aromatic olefins, such as benzene is disclosed as follows:

(1) Hydrogenation in the presence of alkali metal using liquid ammonia as medium, such as disclosed in U.S. Pat. Nos. 3,274,272, 3,321,539, Japan patent Nos. 406,864, 406,865 and 438,102. The drawback of this process is that the used liquid ammonia and alkali metal must be recovered.

(2) Hydrogenation under the catalytic action of ruthenium catalyst using lower alkanols as solvents, such as disclosed in U.S. Pat. No. 3,391,206. The drawback of this process is that the selectivity of cyclohexene is very low.

(3) Hydrogenation under the catalytic action of the ruthenium catalyst in a neutral or acid aqueous solution of a chloride or the sulfates of the metals of groups Ia or IIa of the Periodic Table, magnesium or zinc, such as disclosed in Japan patent No. 5198243. However, the drawback of this process is that the selectivity of cyclohexene is very low.

(4) Hydrogenation under the catalytic action of ruthenium catalyst in an aqueous solution containing carbonates of cobalt, nickel or copper, such as disclosed in Japan patent No. 5346939. However, the drawback of this process is that the selectivity of cyclohexene is very low.

(5) Hydrogenation under the catalytic action of at least one metal selected from Group VIII of the Periodic Table in the basic solution containing water and additives, such as disclosed in U.S. Pat. No. 3,767,720. Although the product yield is high, large amounts of additives and basic solution are needed, and the metal ions on the carrier are easily dissolved out in the base solution.

(6) Hydrogenation under the catalytic action of ruthenium, rhodium or palladium catalyst in the additives-containing basic solution, such as zinc chloride, titanium chloride, etc. containing basic solution and organic benzene solution, such as disclosed in NL patent 7,205,832.

(7) Partial hydrogenation of benzene under the catalytic action of ruthenium-iron alloy, for example cobalt, iron or nickel impregnated onto $Al_2O_3$ in the presence of water, such as disclosed in U.S. Pat. Nos. 3,793,383, 3,912,787 and 4,401,640. The yield of cyclohexene using this process is 18% at maximum.

(8) Hydrogenation under the catalytic action of ruthenium-iron, cobalt-copper or silver/$BASO_4$ in an aqueous solution of cobalt, iron or zinc sulfate, such as disclosed in U.S. Pat. No. 4,575,572 and European patent Nos. 170,915 and 214,530. The process of preparing the catalyst used in this process is very complex, and the characteristic uniformity of the catalyst cannot be easily maintained.

(9) Hydrogenation under the catalytic action of super fine metal catalysts, for example ruthenium, ruthenium-iron or ruthenium-zinc in an aqueous solution of zinc sulfate or hydroxide, such as disclosed in Japan patent Nos. 62201830 and 624544. The drawback of this process is that the recovery and separation of the catalyst are difficult.

(10) Hydrogenation under the catalytic action of ruthenium catalyst composed of a rare earth element compound solid carrier, such as an oxide, hydroxide or carboxide of lanthanum, cerium or praseodymium, and a ruthenium component supported thereon, such as disclosed in U.S. Pat. No. 4,678,861.

(11) Hydrogenation under the catalytic action of a ruthenium-containing solid catalyst in an aqueous solution. The ruthenium-containing solid catalyst is prepared by the hydrolysis and gelation of an alkoxide of silicon or aluminum in a solution containing a ruthenium compound, for example ruthenium alkoxide.

The object of the present invention is to provide a noble metal catalyst, ruthenium catalyst, which could partially hydrogenate aromatic olefins, for example benzene to prepare cyclohexene. Compared with the above references, the catalyst according to the present invention possesses a higher yield and selectivity. According to the present invention, except that a minor alkali solution should be added, other metal salts are not required. Thus, the present invention is simpler in operation.

Catalyst

The present invention uses ruthenium as an active metal, and gallium oxide and zinc oxide as a carrier. The carrier is prepared with a co-precipitation process by mixing an aqueous solution of lanthanum and zinc nitrates in an adequate atomic ratio, followed by adding an adequate carbonate aqueous solution at an elevated temperature and disturbing to precipitate, then sintering for 5 hours after washing and drying so as to confirm the catalyst structure.

(1) Incipient wetness impregnation: this process comprises completely dissolving an amount of $RuCl_3.3H_2O$ into pure water in an amount of the volume required to form incipient wetness, slowly dripping onto the carrier and disturbing at the same time. Due to capillarity, the ruthenium-containing solution is adsorbed into the pores on the carrier. Then, the carrier stands for 2 hours at room temperature, and is dried at 100° C. overnight.

(2) Wetness impregnation: a 20 g carrier is added to a liter of pure water. During disturbing, a 1% Ru aqueous solution is added, and further disturbing for 2 hours. The mixture stands until a dark brown color disappears, then is filtered, washed and dried (@ 80° C., overnight) for the next use.

(3) Catalyst reduction: the impregnated and dried catalyst is weighted and put into a three-hole flask in a ratio of 10 g solid powder/100 ml water. In an atmosphere of $N_2$, $NaBH_4$ is added to separate batches. Disturbing is continued for 1 hour, then the mixture is filtered, dried (@ 80° C., 6hrs) for storage. Because the chlorine ion of ruthenium chloride ($RUCl_3.3H_2O$) is considered to be harmful to the activity of the catalyst, it is necessary that the chlorine ion cannot be detected in the washing filtrate. Adequate composition of the catalyst comprises 1%–5% wt. Ru. The source for the ruthenium ion is preferable from ruthenium chloride or nitride.

Process

The catalyst according to the present invention is prepared by adding adding pure water and adequate alkaline solution. The hydrogen pressure of preparing the present catalyst is 20–100 $kg/cm^2$, and the amount of added alkaline solution is in an amount that can maintain the concentration of aqueous solution between 0.2–1M. The total amount of added pure water is 0.2–2 times the benzene volume. The conversion and selectivity of benzene are defined as follow:

Conversion (%)=the moles of benzene consumed/the total moles of benzene supplied;

Selectivity (%)=the moles of cyclohexene produced/the total moles of benzene consumed.

The degree of hydrogenation and the selectivity of cyclohexene according to the present process depend on the features of used catalyst, the nature of the raw materials and the reaction conditions. The reaction products of the benzene hydrogenating comprise unreacted benzene, partially hydrogenated cyclohexene and fully hydrogenated cyclohaxane. The products could be separated with GC/FID under adequate conditions. Adequate conditions for GC/FID comprise (1) column:column length: 4.5M, ⅛", 10T polyethylene glycol phenyl ether on $^{80}/_{100}$ mesh Chromorb PAW, stainless column; (2) operation conditions: the injected amount of the sample is 1 ml, the temperature of the injector is 150° C., the detector temperature is 170° C., the oven temperature is 70° C., the carrier gas is $N_2$, and the column pressure is 1.4 bar; (3) retention time of each component: cyclohexane: 6 min., cyclohexene: 8.9 min., and benzene: 18.5 min; (4) quantitative calibration: the FID response of each component at the same conditions is different, thus calibration is required; equal amounts of benzene, cyclohexene and cyclohexane are charged into a sample vial. After completely mixing, the mixture is injected to a GC under the above conditions. The response parameter of each component is as follows: benzene: 0.937045, cyclohexene: 1.0113852 and cyclohexane: 1.056235; (6) resultant calculation: the GC area of each component is treated by the Data System of Shin-Hwa Computer.

GC area of benzene x response parameter of benzene=A

GC area of cyclohexene x response parameter of cyclohexene=B

GC are of cylcohexane x response parameter of cyclohexane=C

Benzene wt. %=A/(A+B+C)×100%=P
Cyclohexene wt. %=B/(A+B+C)×100%=Q
Cyclohexane wt. %=C/(A+B+C)×100%=R
Conversion of benzene=1-P
Selectivity of cyclohexene=Q/1-P
Yield of cyclohexene=Q

EXAMPLE 1

Preparation of Bi-Oxide of Gallium Oxide and Zinc Oxide According to the Present Invention 30 grams of gallium nitrate and 18 grams of zinc nitrate are stirred into 500 ml distilled water. After being well stirred and mixed, the mixture is warmed up to 70° C., and a pre-formulated 30% aqueous solution of sodium sulfate is added into the mixture in drops until the litmus test paper changes from red to blue. At this time, a bi-oxide is gradually crystallized and precipitated. The mixture is further stirred for an hour, then is cooled. After being filtered, the precipitated bi-oxide is washed with distilled water, and put into an oven to dry overnight. Then, under room temperature, the dried bi-oxide is put into a sintering furnace, and the temperature is raised by 10° C./min to 500° C., and lasts for 5 hours. 18.8 grams of bi-oxide is obtained. Further bi-oxides of gallium oxide and zinc oxide in different atomic ratios are prepared in the same way.

EXAMPLE 2

Preparation of Catalyst A (2 wt. % Ru)

0.883 g ruthenium chloride is dissolved in 13.8 ml distilled water. After being completely stirred and dissolved, the mixture is added onto 18.8 g bi-oxide of example 1 in drops. After being completely stirred, it stands for 2 hours, then is put into an oven at 80° C. overnight to dry. After being dried, the catalyst is dissolved into 200 ml distilled water, and 5.5 g sodium hydroxide is added in a small portion to reduce the catalyst. After being washed with water and filtered, the catalyst is put into an oven at 80° C. to dry for 6 hours.

EXAMPLE 3

Assay of Reactivity and Selectivity of the Catalyst According to the Present Invention in Hydrogenating Benzene The reactivity and selectivity of the catalyst in partial hydrogenation of benzene is tested according to the following example:

2.48 g sodium hydroxide is stirred and dissolved into 100 ml distilled water, then the mixture is injected into a 300 ml high pressure reactor, and 75 ml benzene and 2.5 g catalyst are added. The partial pressure of hydrogen is 3.72 Mpa, and the reaction temperature is 150° C. The hydrogenation is processed in a batch mode.

Reaction result: (the atomic ratio between gallium and zinc=1:1)

| Reaction time (min) | Benzene Conversion (%) | Cyclohexene Selectivity (%) | Cyclohexene Yield (%) |
| --- | --- | --- | --- |
| 20 | 23.46 | 85.43 | 20.04 |
| 80 | 60.74 | 72.34 | 43.93 |
| 140 | 80.03 | 54.23 | 43.40 |

EXAMPLE 4

The procedure of example 3 is repeated, but the atomic ratio between gallium zinc is 1:5)

| Reaction time (min) | Benzene Conversion (%) | Cyclohexene Selectivity (%) | Cyclohexene Yield (%) |
| --- | --- | --- | --- |
| 20 | 22.43 | 82.43 | 18.49 |
| 80 | 60.41 | 65.48 | 39.56 |
| 140 | 80.12 | 53.19 | 42.62 |

EXAMPLE 5

The procedure of example 3 is repeated, but the atomic ratio between gallium zinc is 2:1)

| Reaction time (min) | Benzene Conversion (%) | Cyclohexene Selectivity (%) | Cyclohexene Yield (%) |
| --- | --- | --- | --- |
| 20 | 19.62 | 84.25 | 16.53 |
| 80 | 51.34 | 68.41 | 35.12 |
| 140 | 69.23 | 51.23 | 35.46 |

Comparative Example 1

The procedure of example 3 is repeated, but the catalyst carrier is gallium oxide

| Reaction time (min) | Benzene Conversion (%) | Cyclohexene Selectivity (%) | Cyclohexene Yield (%) |
| --- | --- | --- | --- |
| 20 | 31.42 | 30.12 | 9.46 |
| 60 | 61.13 | 17.23 | 10.53 |
| 120 | 99.48 | 6.89 | 6.85 |

Comparative Example 2

The procedure of example 3 is repeated, but the catalyst carrier is zinc oxide

| Reaction time (min) | Benzene Conversion (%) | Cyclohexene Selectivity (%) | Cyclohexene Yield (%) |
| --- | --- | --- | --- |
| 20 | 26.83 | 25.53 | 6.85 |
| 60 | 58.76 | 11.95 | 7.02 |
| 100 | 79.7 | 10.95 | 8.73 |

EXAMPLE 6

The procedure of example 3 is repeated but the atomic ratio between gallium zinc in the catalyst carrier is 1:5, the reaction temperature is 133° C. Reaction Result (the atomic ratio of gallium: zinc=1:5)

| Reaction time (min) | Benzene Conversion (%) | Cyclohexene Selectivity (%) | Cyclohexene Yield (%) |
|---|---|---|---|
| 20 | 8.47 | 88.42 | 7.49 |
| 80 | 20.45 | 82.13 | 16.80 |
| 140 | 30.16 | 80.62 | 24.31 |

EXAMPLE 7

The procedure of example 3 is repeated, but the atomic ratio between gallium zinc in the catalyst carrier is 1:5, the reaction temperature is 175° C. Reaction Result (the atomic ratio of gallium: zinc=1:5)

| Reaction time (min) | Benzene Conversion (%) | Cyclohexene Selectivity (%) | Cyclohexene Yield (%) |
|---|---|---|---|
| 20 | 27.41 | 76.23 | 20.89 |
| 80 | 60.32 | 61.49 | 37.09 |
| 140 | 71.25 | 49.34 | 35.15 |

Although the present invention has been described with reference to preferred embodiments, the embodiment is only for the purpose of putting on a demonstration rather than limiting the invention. Workers skilled in the art will recognize that changes may be made in form and detail without departing from the spirit or essential attributes thereof.

What is claimed is:

1. A catalyst suitable for partially hydrogenating aromatic olefins, comprising a metallic active component selected from the group consisting of metals of Group VIII of the Periodic Table deposited on a bi-oxide of gallium oxide-zinc oxide, wherein the atomic ratio of gallium and zinc in the bi-oxide is from 1:1 to 1:5.

2. A catalyst according to claim 1, wherein the metallic active component is ruthenium.

3. A catalyst according to claim 1, wherein the metallic active component is reduced by a sodium hydroboron in an aqueous solution.

4. A catalyst according to claim 1, wherein the atomic ratio of gallium and zinc in the bi-oxide is 1:1.

5. A catalyst according to claim 1, wherein the atomic ratio of gallium to zinc in the bi-oxide is 1:5.

6. A catalyst according to claim 2, wherein the metallic active component is reduced by a sodium hydroboron in an aqueous solution.

7. A catalyst according to claim 2, wherein the atomic ratio of gallium and zinc in the bi-oxide is 1:1.

8. A catalyst according to claim 2, wherein the atomic ratio of gallium to zinc in the bi-oxide is 1:5.

* * * * *